(12) United States Patent
Davis, Jr.

(10) Patent No.: US 7,549,997 B2
(45) Date of Patent: Jun. 23, 2009

(54) BODY CANAL DILATION SYSTEM

(76) Inventor: Thomas William Davis, Jr., 13239 Hunters Creek, College Station, TX (US) 77845

( * ) Notice: Subject to any disclaimer, the term of this patent is extended or adjusted under 35 U.S.C. 154(b) by 0 days.

(21) Appl. No.: 10/856,967

(22) Filed: May 28, 2004

(65) Prior Publication Data

US 2005/0267509 A1  Dec. 1, 2005

(51) Int. Cl.
*A61M 29/00* (2006.01)
(52) U.S. Cl. .................................... 606/193
(58) Field of Classification Search ............... 604/515, 604/514, 517, 264, 523, 533, 544, 104–109, 604/912, 915, 918, 920, 96.01–103.14; 606/191, 606/192, 193, 194, 195, 197, 198
See application file for complete search history.

(56) References Cited

U.S. PATENT DOCUMENTS

| | | | | |
|---|---|---|---|---|
| 3,587,588 A * | 6/1971 | Murr | ................ | 606/191 |
| 3,721,229 A * | 3/1973 | Panzer | ................ | 600/435 |
| 3,948,270 A * | 4/1976 | Hasson | ................ | 604/515 |
| 4,349,033 A * | 9/1982 | Eden | ................ | 600/458 |
| 4,467,816 A * | 8/1984 | Schluter et al. | ........... | 600/569 |
| 5,158,543 A * | 10/1992 | Lazarus | ................ | 604/164.1 |
| 5,197,971 A * | 3/1993 | Bonutti | ................ | 606/192 |
| 5,248,304 A * | 9/1993 | Vigdorchik et al. | ... | 604/278 |
| 5,259,836 A * | 11/1993 | Thurmond et al. | ...... | 600/431 |
| 5,338,297 A * | 8/1994 | Kocur et al. | ......... | 604/103.03 |
| 5,368,598 A * | 11/1994 | Hasson | ................ | 606/119 |
| 5,372,584 A * | 12/1994 | Zink et al. | ............ | 604/515 |
| 5,376,084 A * | 12/1994 | Bacich et al. | ......... | 604/515 |
| 5,624,399 A * | 4/1997 | Ackerman | ........ | 604/103.03 |
| 5,846,259 A * | 12/1998 | Berthiaume | ......... | 606/192 |
| 5,897,551 A * | 4/1999 | Everett et al. | ......... | 606/15 |
| 5,935,098 A * | 8/1999 | Blaisdell et al. | ........ | 604/515 |
| 6,080,129 A * | 6/2000 | Blaisdell | ............ | 604/515 |
| 6,802,825 B2 * | 10/2004 | Ackerman et al. | ..... | 604/174 |
| 6,827,703 B1 * | 12/2004 | Ackerman | ........... | 604/96.01 |
| 2005/0080443 A1 * | 4/2005 | Fallin et al. | ............ | 606/191 |
| 2005/0149101 A1 * | 7/2005 | Huschmand Nia | ..... | 606/193 |

FOREIGN PATENT DOCUMENTS

DE  10208508  * 1/2003

* cited by examiner

*Primary Examiner*—Nicholas D Lucchesi
*Assistant Examiner*—Christopher D Koharski

(57) ABSTRACT

An apparatus and method for dilating a body canal such as a cervix is provided. The apparatus includes a threaded cylindrical rod with an inflatable member at one end. The apparatus also includes a tubular member with a threaded bore that is capable of threaded engagement with the threaded rod.

27 Claims, 4 Drawing Sheets

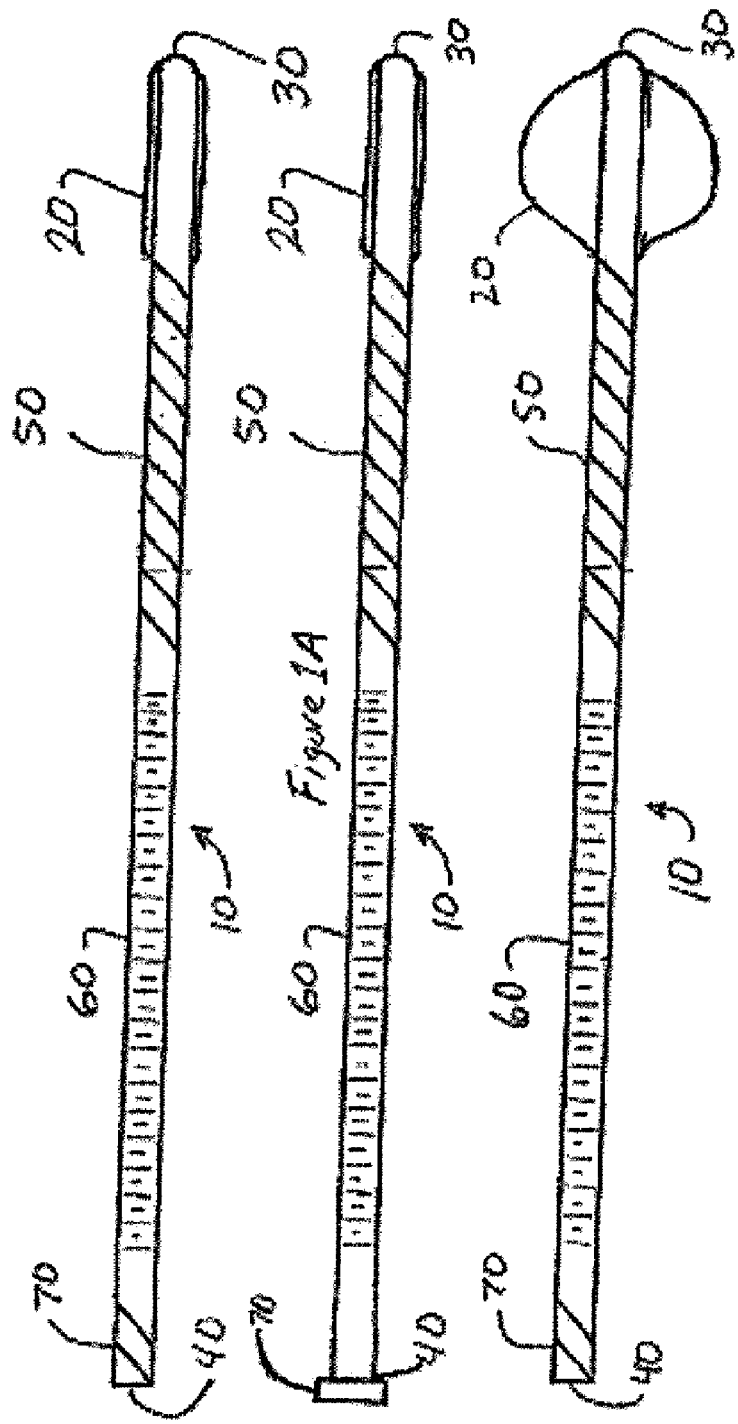

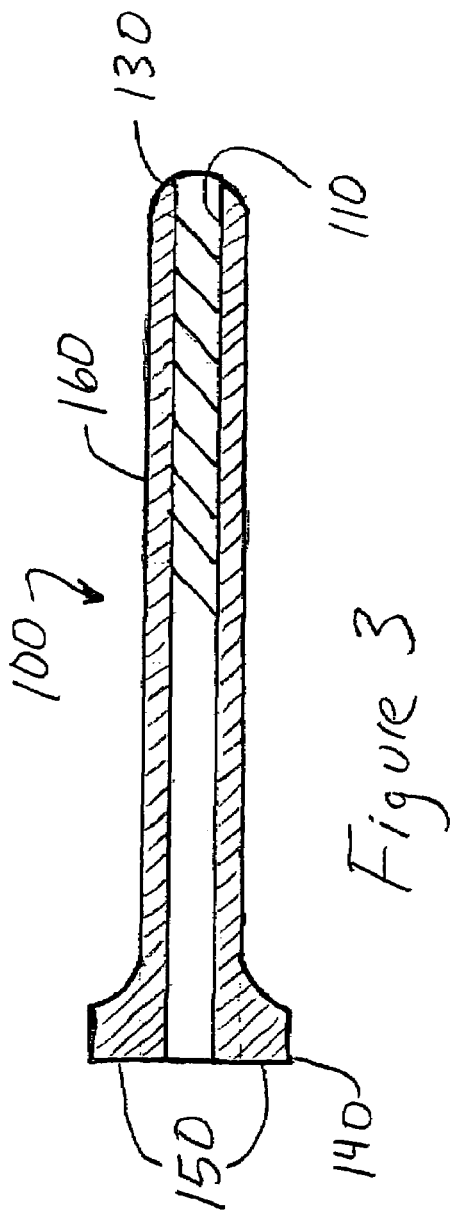
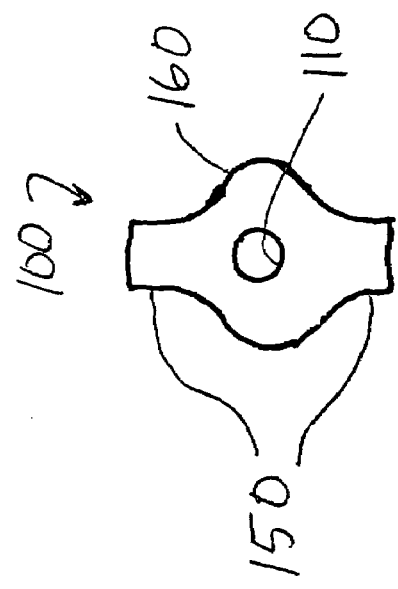

BODY CANAL DILATION SYSTEM

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates generally to a system for dilating a body canal such as a cervix. In one aspect, and more particularly, the invention relates to a system for dilating a cervix comprising a cylindrical rod with an inflatable member disposed on one end. Still more particularly, the invention relates to a system for dilating a cervix comprising a tubular member that is capable of threaded engagement with the cylindrical rod.

2. Description of the Related Art

A common system for dilating a cervix in the existing art involves the use of long metal rods. A rod of smaller diameter is inserted into the cervix and advanced until it reaches the uterine cavity. The rod is then removed and a larger diameter metal rod is inserted in a similar fashion. The process is repeated until the cervix has been dilated to the desired size. This process has several disadvantages.

One disadvantage is that the person performing the dilation procedure cannot insert the metal rod in a controlled manner. This procedure requires that a force be applied in the direction of insertion by the person performing the procedure. If there is a change in the resistance, the rod may be accidentally inserted farther than desired. Furthermore, there is nothing in these systems to prevent the dilating rod from being inserted into the uterine cavity. This can cause soft tissue damage or other injuries to the cervical or uterine cavities, such as cervical lacerations or uterine perforations. Injuries such as these may lead to increased blood loss, infection, and overall recovery time. Therefore, it is desired that such injuries be avoided whenever possible.

A further disadvantage of existing dilation systems such as those described above is that the person performing the dilating procedure has no way of knowing how far the rod has been inserted or if it has extended beyond the cervix and into the uterine cavity.

SUMMARY OF PREFERRED EMBODIMENTS OF INVENTION

Preferred embodiments of the present invention are disclosed as having a cylindrical rod with an inflatable member at one end and a tubular member capable of threaded engagement with the cylindrical rod. Preferred embodiments control the insertion of the tubular member by threaded engagement between the tubular member and cylindrical rod. Preferred embodiments also utilize the inflatable member to prevent the tubular member from being inserted past a desired point. Preferred embodiments also comprise graduated markings on the cylindrical rod to allow the person performing the procedure to know how far the cylindrical rod or tubular member has been inserted.

Thus, the embodiments of the cervical dilation system summarized above comprise a combination of various features and advantages that enable the system to overcome various problems of prior devices. Preferred embodiments of the present invention will allow more user control while also decreasing the risk of uterine perforation, cervical laceration, and soft tissue injury. This decrease in complication will lower surgical morbidity by decreasing infection, blood loss and overall recovery time. Preferred embodiments of the present invention may be utilized in any procedure that requires access to a body cavity such as the intrauterine cavity. Such procedures include diagnostic hysteroscopy, operative hysteroscopy, and dilation with suction or curettage. The various characteristics mentioned above, as well as other features and characteristics described in more detail below, will be readily apparent to those skilled in the art upon reading the following detailed description of preferred embodiments, and by referring to the accompanying drawings.

BRIEF DESCRIPTION OF THE DRAWINGS

For a more detailed description of the preferred embodiment of the present invention, reference will now be made to the accompanying drawings, wherein:

FIG. 1 is a side view of a threaded cylindrical rod with an inflatable member (prior to inflation) attached to one end.

FIG. 1A is an alternative embodiment of the cylindrical rod of FIG. 1.

FIG. 2 is a side view of a threaded cylindrical rod with an inflatable member (after inflation) attached to one end.

FIG. 3 is a section side view of a tubular member.

FIG. 4 is an end view of the tubular member shown in FIG. 2.

DETAILED DESCRIPTION OF THE PREFERRED EMBODIMENT

Figure 5:
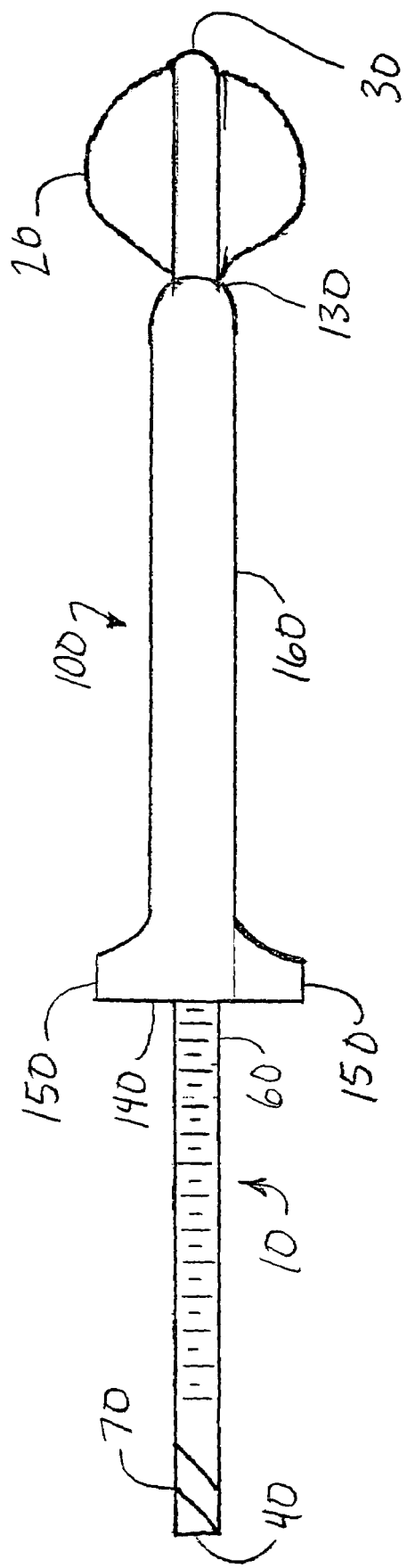
FIG. 5 is an assembly view of the tubular member shown in FIG. 2 disposed on the threaded cylindrical rod shown in FIG. 1.
Figure 6:
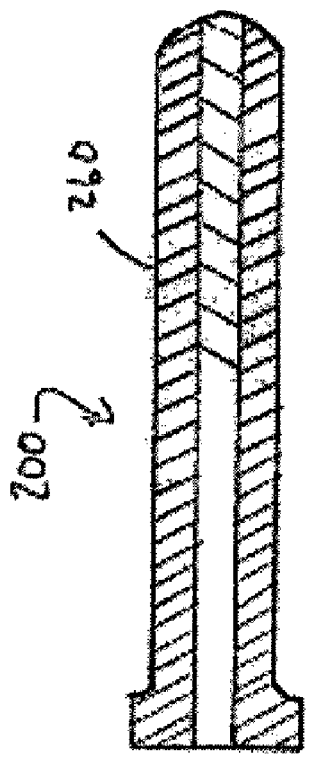
FIG. 6 is a section side view of a second tubular member.
Figure 7:
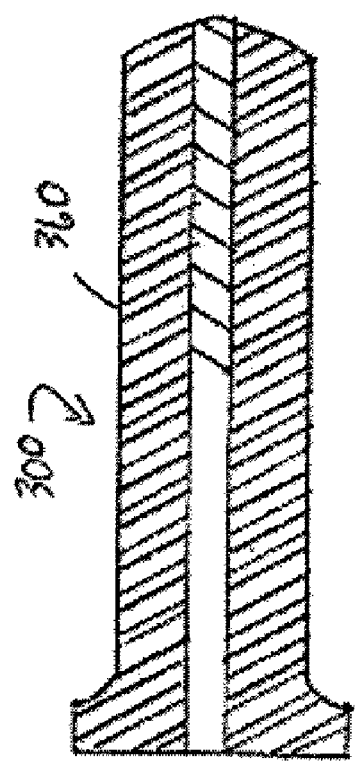
FIG. 7 is a section side view of a third tubular member.

It is contemplated that embodiments of the present invention may be utilized to dilate various body canals. However, dilation of a cervix will be discussed below in an exemplary manner.

Referring first to FIG. 1, cylindrical rod 10 comprises inflatable member 20 disposed on first end 30 and opposed to second end 40. Cylindrical rod 10 also comprises threaded portion 50 and graduated markings 60 between first end 30 and second end 40. Second end 40 also comprises connection mechanism 70, such as threads (shown in FIG. 1) or a nipple (shown in FIG. 1A). Preferably, cylindrical rod 10 is 3 mm in diameter and 30 cm in length. With inflatable member 20 in a deflated condition as shown in FIG. 1, first end 30 of cylindrical rod 10 is inserted into a cervix (not shown). Insertion of cylindrical rod 10 is continued until first end 30 extends beyond the cervix and enters the uterus (not shown). Insertion may be continued until first end 30 contacts the fundus (the top of the uterus—not shown) to ensure that first end 30 and inflatable member 20 are past the cervix and in the uterus. Graduated markings 60 may also be used to determine how far cylindrical rod 10 has been inserted and therefore determine the depth of the cervix and uterus.

With inflatable member 20 in the uterus, a Luer Lock syringe (not shown) or other similar device may be connected to connection mechanism 70. The syringe or other inflation device is then used to inflate inflatable member 20, as shown in FIG. 2, by means of an acceptable sterile fluid or gas.

Inflatable member 20 preferably comprises a 15-30 ml bulb or balloon, but devices of other sizes may be used. After inflatable member 20 has been inflated, cylindrical rod 10 is retracted until inflatable member 20 contacts the cervix. Inflatable member 20 in an inflated state is larger in diameter than the cervix and therefore does not enter the cervix. In this position, inflatable member 20 separates the cervix from the uterus. The syringe or inflation device is then removed from second end 40 while inflatable member 20 stays in an inflated condition. Inflatable member 20 preferably comprises a valve or other mechanism that allows it to stay inflated after the syringe or inflation device is removed.

Referring now to FIGS. 3 through 7, tubular member 100 comprises outer surface 160 and threaded bore 110. Tubular member also comprises first end 130 and second end 140 with extensions 150. With cylindrical rod 10 retracted so that inflatable member 20 is in contact with the cervix, tubular member 100 is positioned so that second end 40 of cylindrical rod 10 is disposed within threaded bore 110 near first end 130 of tubular member 100. Tubular member 100 is then moved towards first end 30 of cylindrical rod 10 until threaded bore 110 engages threaded portion 50. Extensions 150 may then be used to rotate tubular member 100 and advance tubular member 100 towards first end 30 of cylindrical rod 10. Because advancement of tubular member 100 is accomplished through engagement of threaded portion 50 and threaded bore 110, the movement may be accomplished in a controlled manner. In addition, inflatable member 20 prevents tubular member 100 from advancing beyond first end 30 of cylindrical rod 10, as shown in FIG. 5. This prevents tubular member 100 from accidentally entering the uterus and potentially causing damage to the uterine cavity. In addition to increasing safety, embodiments of the present invention may also increase patient comfort. The gradual advancement of tubular member 100, as opposed to the potentially abrupt insertion of prior art devices, should decrease the discomfort experienced by the patient.

As tubular member 100 is advanced into the cervix and towards inflatable member 20, outer surface 160 expands or dilates the cervix. First end 130 of tubular member 100 is preferably rounded or tapered to minimize patient discomfort and the chance of injury during advancement. It is also preferred that outer surface 160 is approximately 5 mm in diameter when tubular member 100 is initially inserted into the cervix. This smaller diameter minimizes the chance of damage or injury during the dilation procedure. The person performing the procedure will know that tubular member 100 has been fully inserted when first end 130 of tubular member 100 contacts inflatable member 20. Inflatable member 20 prevents tubular member from being inserted past the cervix and into the uterus, thereby increasing safety and reducing the risk of injury. The person performing the procedure may use the graduated markings to note the distance at which tubular member 100 is fully inserted. After tubular member 100 has been fully inserted, it may then be retracted by turning it in the direction opposite of that used to advance tubular member 100. Tubular member 100 may be retracted to the point that threaded bore 110 is no longer engaged with threaded portion 50. At this point, tubular member 100 may be removed from the cylindrical rod 10. A second tubular member 200 with an outer surface 260 of increased diameter may then be inserted in a similar manner to further dilate the cervix. Preferably, tubular members are 15 cm in length and include diameters of 5 mm, 7 mm, 10 mm, 12 mm, and 14 mm. Tubular members of increasing diameter, such as third tubular member 300 with an outer surface 360 of additionally increased diameter, may be inserted until the cervix reaches the desired size. For example, many medical devices include scopes of 8 or 10 mm diameter and therefore require the cervix to be dilated to such a size. Graduated markings 60 may be used to confirm that subsequent tubular members are fully inserted. When the cervix has reached the desired size and tubular member 100 has been removed, inflatable member 20 may deflated and cylindrical rod 10 may be removed. Inflatable member 20 may be deflated by connecting a syringe or other device to second end 40 and creating a vacuum or suction to deflate inflatable member 20.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the particular embodiments described herein, but is only limited by the claims which follow, the scope of which shall include all equivalents of the subject matter of the claims.

What is claimed is:

1. A method of dilating a body canal comprising:

inserting a cylindrical rod comprising a first end, a second end, and a threaded portion into the body canal;

further inserting the cylindrical rod until said first end exits said body canal and enters a cavity;

inflating an inflatable member disposed on said first end of said cylindrical rod;

retracting said cylindrical rod until said inflatable member contacts said body canal;

disposing a first tubular member comprising a first outer diameter, a threaded bore and a tapered end onto said second end of said cylindrical rod whereby said second end is disposed within said bore;

moving said first tubular member towards said first end of said cylindrical rod until said threaded bore engages said threaded portion;

rotating said first tubular member to threadingly displace said first tubular member in gradual increments towards said first end of said cylindrical rod and into said body canal;

dilating said body canal with said first tubular member;

removing said first tubular member from said cylindrical rod;

disposing a second tubular member comprising a second outer diameter larger than said first outer diameter, a threaded bore and a tapered end onto said second end of said cylindrical rod whereby said second end is disposed within said bore;

moving said second tubular member towards said first end of said cylindrical rod until said threaded bore engages said threaded portion;

rotating said second tubular member to threadingly displace said second tubular member in gradual increments towards said first end of said cylindrical rod and into said body canal; and dilating said body canal with said second tubular member.

2. The method of claim 1 further comprising:

removing said second tubular member from said cylindrical rod;

disposing a third tubular member comprising a third outer diameter larger than said first outer diameter, a threaded bore and a tapered end onto said second end of said cylindrical rod whereby said second end is disposed within said bore;

moving said third tubular member towards said first end of said cylindrical rod until said threaded bore engages said threaded portion;

rotating said third tubular member to threadingly displace said third tubular member in gradual increments towards said first end of said cylindrical rod and into said body canal; and dilating said body canal with said third tubular member.

3. The method of claim 1 whereby said first tubular member is advanced toward said first end of said cylindrical rod until said first tubular member engages said inflatable member.

4. The method of claim 1 whereby said cylindrical rod comprises graduated markings depicting a distance from said first end to said markings of said cylindrical rod, and wherein said first tubular member is advanced along said cylindrical rod a distance measured by said graduated markings.

5. The method of claim 1 whereby said outer surface of said first tubular member is greater than or equal to 4 mm in diameter and less than or equal to 15 mm in diameter.

6. The method of claim 1 whereby said cylindrical rod is greater than or equal to 25 cm in length and less than or equal to 35 cm in length.

7. The method of claim 1 whereby said second end of said cylindrical rod comprises a connection mechanism capable of connecting to an inflation device.

8. The method of claim 7 whereby said inflation device is inflated by a syringe.

9. The method of claim 7 whereby said connection mechanism comprises threads or a nipple.

10. The method of claim 1 whereby said tubular member comprises radial extensions, and wherein said tubular member is advanced along said cylindrical rod by rotating said extensions.

11. The method of claim 10 wherein said outer diameter of said first tubular member is substantially constant between said tapered end and said extensions.

12. The method of claim 1 whereby said cylindrical rod and said first tubular member comprise molded surgical quality plastic.

13. The method of claim 1 whereby said inflatable member is a balloon with a volume greater than or equal to 15 ml and less than or equal to 30 ml.

14. The method of claim 1 whereby the diameter of said inflatable member after inflation is greater than the diameter of said body canal.

15. A method of constructing a device for dilating a body canal comprising:

providing a cylindrical rod comprising a first end, a second end, and a threaded portion;

providing an inflatable member disposed on said first end of said cylindrical rod;

providing a first tubular member comprising a first outer diameter, a tapered end, and a threaded bore for threaded engagement with said threaded portion of said cylindrical rod;

providing a second tubular member comprising a second outer diameter, a threaded bore and a tapered end for threaded engagement with said threaded portion of said cylindrical rod;

whereby said first tubular member is capable of being disposed on said cylindrical rod and is operable to threadingly displace in gradual increments along said cylindrical rod toward said first end and into said body canal, thereby gradually dilating said body canal to a first size;

and whereby said first tubular member is capable of being removed from said threaded portion of said cylindrical rod and replaced by said second tubular member, whereby said second tubular member is capable of being disposed on said cylindrical rod and is operable to threadingly displace in gradual increments along said cylindrical rod toward said first end and into said body canal, thereby gradually dilating said body canal to a second size.

16. An apparatus for dilating a cervix comprising:

a cylindrical rod comprising a first end and a second end;

an inflatable member disposed on said first end of said cylindrical rod;

a threaded portion on said cylindrical rod;

a first tubular member and an additional set of two or more tubular members, wherein each tubular member comprises an outer surface, a rounded end, an opposite end, and a threaded bore, said outer surface of said first tubular member having a first diameter, wherein each tubular member has a substantially constant diameter between said rounded end and said opposite end, wherein said outer surface of each tubular member within said additional set of two or more tubular members has a larger diameter than said first diameter, wherein said additional set comprises two or more tubular members of increasing diameter, and whereby each tubular member is operable to directly thread to said threaded portion on said cylindrical rod, and whereby each tubular member is operable to threadingly displace in gradual increments along said cylindrical rod toward said first end and into said cervix, thereby gradually dilating said cervix.

17. The apparatus of claim 16 whereby said inflatable member prevents said tubular members from extending beyond said first end of said cylindrical rod.

18. The apparatus of claim 16 whereby said cylindrical rod includes graduated markings indicating a distance from said first end to said markings of said cylindrical rod.

19. The apparatus of claim 16 whereby said outer surface of each tubular member is greater than or equal to 4 mm in diameter and less than or equal to 15 mm diameter.

20. The apparatus of claim 16 whereby said cylindrical rod is greater than or equal to 25 cm in length and less than or equal to 35 cm in length.

21. The apparatus of claim 16 whereby said second end of said cylindrical rod includes a connection mechanism capable of connecting to an inflation device.

22. The apparatus of claim 21 whereby said inflation device is a syringe.

23. The apparatus of claim 21 whereby said connection mechanism comprises threads or a nipple.

24. The apparatus of claim 16 whereby each tubular member further comprises radial extensions spaced from said rounded end and adapted to assist in rotating said tubular member and advancing said tubular member along said cylindrical rod.

25. The apparatus of claim 16 whereby said cylindrical rod and each tubular member comprise molded surgical quality plastic.

26. The apparatus of claim 16, whereby said inflatable member is a balloon with a volume greater than or equal to 15 ml and less than or equal to 30 ml.

27. The apparatus of claim 16 wherein said additional set of two or more tubular members includes tubular members with increasing diameters ranging from about 5 mm to about 14 mm.

* * * * *